US009006140B2

(12) United States Patent
Panicheva et al.

(10) Patent No.: US 9,006,140 B2
(45) Date of Patent: Apr. 14, 2015

(54) FLORAL PRESERVATIVE

(75) Inventors: Svetlana Panicheva, Downingtown, PA (US); Mark N. Sampson, Doylestown, PA (US)

(73) Assignee: PuriCore, Inc., Malvern, PA (US)

( * ) Notice: Subject to any disclaimer, the term of this patent is extended or adjusted under 35 U.S.C. 154(b) by 0 days.

(21) Appl. No.: 12/845,046

(22) Filed: Jul. 28, 2010

(65) Prior Publication Data

US 2011/0028319 A1 Feb. 3, 2011

Related U.S. Application Data

(60) Provisional application No. 61/229,163, filed on Jul. 28, 2009.

(51) Int. Cl.
*A01N 3/00* (2006.01)
*A01N 59/08* (2006.01)
*C05D 1/02* (2006.01)
*A01N 59/00* (2006.01)
*A01N 3/02* (2006.01)
*C02F 1/467* (2006.01)

(52) U.S. Cl.
CPC *A01N 59/00* (2013.01); *A01N 3/00* (2013.01); *C05D 1/02* (2013.01); *A01N 59/08* (2013.01); *A01N 3/02* (2013.01); *C02F 1/4674* (2013.01); *C02F 2201/46115* (2013.01)

(58) Field of Classification Search
None
See application file for complete search history.

(56) References Cited

U.S. PATENT DOCUMENTS

| 3,287,104 | A | * | 11/1966 | Biggs | 504/115 |
|---|---|---|---|---|---|
| 4,278,715 | A | | 7/1981 | Romero-Sierra et al. | |
| 5,080,707 | A | | 1/1992 | Ide et al. | |
| 5,171,351 | A | * | 12/1992 | Yamamoto et al. | 504/114 |
| 5,213,604 | A | * | 5/1993 | Saito et al. | 504/114 |
| 5,284,818 | A | | 2/1994 | Shafer et al. | |
| 5,366,954 | A | | 11/1994 | Bestwick et al. | |
| 5,421,121 | A | | 6/1995 | Bestwick et al. | |
| 5,500,403 | A | | 3/1996 | Shafer et al. | |
| 5,536,155 | A | | 7/1996 | Futaki et al. | |
| 5,580,840 | A | | 12/1996 | Harms et al. | |
| 5,599,571 | A | * | 2/1997 | Estrada | 426/321 |
| 5,635,443 | A | | 6/1997 | Lesenko | |
| 5,679,617 | A | * | 10/1997 | Hanafusa et al. | 504/115 |
| 5,723,406 | A | | 3/1998 | Larose et al. | |
| 5,817,600 | A | | 10/1998 | Carstairs et al. | |
| 5,961,886 | A | | 10/1999 | Hashimoto et al. | |
| 6,440,900 | B1 | | 8/2002 | Koermer et al. | |
| 7,144,841 | B2 | | 12/2006 | Pius | |
| 7,199,082 | B1 | | 4/2007 | Chapman et al. | |
| 7,273,831 | B1 | | 9/2007 | Fleskes et al. | |
| 7,345,008 | B1 | | 3/2008 | Suzuki et al. | |

| 2006/0140998 | A1 | | 6/2006 | Nakanishi et al. | |
|---|---|---|---|---|---|
| 2007/0231247 | A1 | * | 10/2007 | Bromberg et al. | 423/473 |
| 2009/0008268 | A1 | * | 1/2009 | Salathe et al. | 205/746 |

FOREIGN PATENT DOCUMENTS

| DE | 10 2006 0432647 | 3/2008 |
|---|---|---|
| WO | WO 03/075638 | 9/2003 |
| WO | WO 2004/027116 | 4/2004 |

OTHER PUBLICATIONS

Excerpt of Oxford Dictionary of Chemistry (2004), Potassium Chlorate, p. 457.*
Kemme, Preserving Cut Flowers, University of Illinois Extension Master Gardener News Column (2007).*
Harada, Behavior of Hydrogen Peroxide in Electrolyzed Anode Water, Biosci., Biotechnol., Biochem. (2002), vol. 66, No. 9, pp. 1783-1791.*
Reid, Cut Flowers and Greens, Department of Environmental Horticulture, University of California, Davis, CA (2001).*
Anwar-Ul-Haq et al, "Effect of Nitrogen, Phosphorus and Potassium on Vegetative and Reproductive Growth of Rose (*Rosa centifolia*)" International Journal of Agriculture & Biology, vol. 1, No. 1 / 2 (1999) 27-29.
Clark et al, "Efficacy of super-oxidized water fogging in environmental decontamination" Journal of Hospital Infection 64 (2006) 386-390.
Gast, Karen L.B. "Postharvest Handling of Fresh Cut Flowers and Plant Material" http://www.ksre.ksu.edu/library/hort2/mf2261.pdf Kansas State University Agricultural Experiment Station and Cooperative Extension Service (May 1997) 1-12.
Kates et al., "Indigenous multiresistant bacteria from flowers in hospital and nonhospital environments" American Journal of Infection Control, vol. 19, No. 3, Jun. 1991, 156-161.
Larson, Roy A. (editor), Introduction to Floriculture Second Edition, Academic Press, Inc. San Diego, CA (1980, 1992) pp. 11, 13, 51, 79, 88 and 91.
Loshon et al., "Analysis of the killing of spores of *Bacillus subtilis* by a new disinfectant, Sterilox®" Journal of Applied Microbiology 91 (2001) 1051-1058.
Martin and Gallagher "An investigation of the efficacy of super-oxidised (Optident/Sterilox) water for the disinfection of dental unit water lines" British Dental Journal vol. 198, No. 6 (Mar. 26, 2005) 353-354.
Melly et al., "Analysis of the properties of spores of *Bacillus subtilis* prepared at different temperatures" Journal of Applied Microbiology 92 (2002) 1105-1115.
Middleton et al, "Comparison of a solution of super-oxidized water (Sterilox®) with glutaraldehyde for the disinfection of bronchoscopes, contaminated in vitro with *Mycobacterium tuberculosis* and *Mycobacterium avium-intracellulare* in sputum" Journal of Hospital Infection 45 (2000) 278-282.
Park et al, "Evaluation of Liquid- and Fog-Based Application of Sterilox Hypochlorous Acid Solution for Surface Inactivation of Human Norovirus" Applied and Environmental Microbiology, vol. 73, No. 14 (May 2007) 4463-4468.

(Continued)

*Primary Examiner* — Abigail Fisher
*Assistant Examiner* — Frank Choi
(74) *Attorney, Agent, or Firm* — Stradley Ronon Stevens & Young, LLP

(57) ABSTRACT

An electrochemically treated solution and method for cut flower and plant preservation, the solution having potassium, hypochlorous acid, and dissolved oxygen.

16 Claims, No Drawings

(56) References Cited

OTHER PUBLICATIONS

Pineau, Lionel "Etude 99-E-229 Sterilox/Lancer Preliminary Report" (1999) 1-6.
Selkon et al. "Evaluation of the antimicrobial activity of a new super-oxidized water, Sterilox®, for the disinfection of endoscopes" Journal of Hospital Infection 41 (1999) 59-70.
Selkon, J.B., "Development of a New Antiseptic for Treating Wound Infection" The Oxford European Wound Healing Course Handbook. Wound Healing Institute, Oxford, England (2002) 159-164.
Shetty et al. "Evaluation of microbicidal activity of a new disinfectant: Sterilox® 2500 against *Clostridium difficile* spores, *Helicobacter pylori*, vancomycin resistant *Enterococcus* species, *Candida albicans* and several *Mycobacterium* species" Journal of Hospital Infection 41 (1999) 101-105.
Silberbush and Lieth, "Nitrate and potassium uptake by greenhouse roses (*Rosa hybrida*) along successive flower-cut cycles: a model and its calibration" Scientia Horticulturae 101 (2004) 127-141.
Starck et al., "Effect of Fertiliser Nitrogen and Potassium Upon Yield and Quality of Carnations Grown in Peat and Sawdust" Abstract ISHS Acta Horticulturae 294: II Symposium on Horticultural Substrates and their Analysis, XXIII IHC http://www.actahort.org/members/showpdf?booknrarnr=294_31 as downloaded Jul. 23, 2009.
Tapper et al, "Atomic force microscopy study of the biocidal effect of super-oxidised water, Sterilox" Biofilm, vol. 3, Paper 4 (BF98004) (Jul. 10, 1998) Online Journal—URL: http://www.bdt.org.br/bioline/bf (printed from http://www.bioline.org.br/request?bf98004 Aug. 1, 2002) 16 pages (8 text, 8 photographs).
Walker et al., "Microbiological Evaluation of a Range of Disinfectant Products to Control Mixed-Species Biofilm Contamination in a Laboratory Model of a Dental Unit Water System" Applied and Environmental Microbiology vol. 69, No. 6 (Jun. 2003) 3327-3332.
Zinkevich et al. "The effect of super-oxidised water on *Escherichia coli*" Journal of Hospital Infection 46 (2000) 153-156.
International Search Report and Written Opinion dated Dec. 22, 2011 for corresponding international application No. PCT/US2010/043495.
Nakagawara S. et al., "Spectroscopic Characterization and the pH Dependence of Bactericidal Activity of the Aqueous Chlorine Solution" Analytical Sciences, Aug. 1998, vol. 14, The Japan Society for Analytical Chemistry, Tokyo, JP pp. 691-698.
Al-Haq et al, "Applications of Electrolyzed Water in Agriculture & Food Industries" Food Science Technologies Res. 11(2) pp. 135-150 (2005).
Buck et al., "In Vitro Fungicidal Activity of Acidic Electrolyzed Oxidizing Water" Plant Disease vol. 86, No. 3, pp. 278-281 (Mar. 2002).
Hur et al., "Inhibitory Effects of Super Reductive Water on Plant Pathogenic Fungi" Plant Pathology Journal 18(5); pp. 284-287 (2002).
van Doom et al., "Effects of surfactants on the longevity of dry-stored cut flowering stems of rose, *Bouvardia*, and *Astilbe*" Postharvest Biology and Technology vol. 3, Issue 1, Jul. 1993, pp. 69-76 (Abstract Only).
Ruting, A. "Effects of Wetting Agents and Cut Flower Food on the Vase Life of Cut Roses" ISHS Acta Horticulturae 298: Hortifroid, V International Symposium on Postharvest Physiology of Ornamental Plants; Importance of Cold in Ornamental Horticulture (Dec. 1, 1991) (Abstract Only).
van Doorn et al., "Alkylethoxylate surfactants for rehydration of roses and *Bouvardia* flowers" Postharvest Biology and Technology vol. 24, Issue 3, Apr. 2002, pp. 327-333 (Abstract Only).
van Doorn et al., "Effect of antimicrobial compounds on the number of bacteria in stems of cut rose flowers" Journal of Applied Bacteriology 1990, 68, 117-122.
Jones et al., Pulsing with Triton X-100 Improves Hydration and Vase Life of Cut Sunflowers (*Helianthus annuus* L) HortScience 28(12): 1178-1179, 1993.
de la Riva et al., "Treatment with Peracetic Acid Extends the Vase Life of Lisianthus (*Eustoma grandiflorum*) Flowers" HortScience 44(2): 418-420 (2009).
van Doorn "Vascular Occlusion in Stems of Cut Rose Flowers" Ph.D. Thesis, Agricultural University, Wageningen, The Netherlands 154 pages ISBN90-5485-139-2 (1993).
Excerpt (Mar. 7, 2011) from Oxford Dictionary of Chemistry (2004), "Potassium Chlorate", p. 457.†
Excerpt (Mar. 7, 2011) from KEMME, Preserving Cut Flowers, University of Illinois Extension (Feb. 13, 2007).†

* cited by examiner

FLORAL PRESERVATIVE

CROSS REFERENCE TO RELATED APPLICATIONS

This application claims the benefit of U.S. Provisional Application No. 61/229,163, filed Jul. 28, 2009, the contents of which are incorporated in this application by reference.

BACKGROUND OF THE INVENTION

The invention relates to a preservative or watering solution for cut flowers and plants during their storage life. In particular, the invention relates to an electrochemically treated solution that extends the life of cut flowers and plants and prevents biofouling of the stems.

Fresh cut flowers begin to loose their freshness as soon as they are cut. As such, there is a desire among floral retailers and consumers to lengthen their lifetime. Adding preservatives to water in which the fresh cut flowers are stored is a common practice. These preservatives range from powders to slurries to liquids of various ingredients. Many of the current preservatives do not provide biocide or odor control for flower and vase solutions and the addition of disinfectants is often needed.

SUMMARY OF THE INVENTION

One aspect of this invention provides an electrochemically treated solution for cut flower and plant preservation comprising at least 99.5% by weight water, potassium, no more than 0.01% by weight hypochlorous acid, and dissolved oxygen.

Another aspect of the invention provides an electrochemically treated solution for cut flower and plant preservation comprising at least 99.5% by weight water, no more than 0.3% by weight potassium chloride, no more than 0.01% by weight hypochlorous acid, and no more than 0.001% by weight dissolved oxygen. The solution has a pH of about 2.5 to 8 and a conductivity of about 0.2-18 mS.

Yet another aspect of the invention provides a method of extending cut flower and plant life comprising providing an electrochemically treated aqueous solution having potassium, hypochlorous acid and dissolved oxygen and immersing a stem in the electrochemically treated aqueous solution.

DETAILED DESCRIPTION OF THE INVENTION

The invention provides an electrochemically treated solution used to treat cut flowers and plants, including non-flowering plants that are used in bouquets and other flower arrangements, and even cut trees and tree branches. Reference to cut flowers throughout the application also includes non-flowering plants. The solution provides an energy source for cut flowers and plants, for example, by supplying the plants with macro-nutrients, such as potassium. Furthermore, the antimicrobial solution controls biofouling in floral storage solution and biofilm growth on the stems of flowers, retarding floral spoilage and protecting stems from rotting. The solution also prevents slime accumulation on the walls of storage containers and reduces the need for cleaning of those containers.

The solution is a preservative or watering solution for cut flowers that extends their storage life, which is the time the cut flowers are kept in cold storage at a retailer or wholesaler, and their vase life, which is the time a cut flower lasts in a customer's home. As a result, the flower is prolonged and the freshness of the flower is maintained over a longer period of time than if the flower was not in the solution or in water alone.

A fresh cut flower is still a living specimen even though it has been cut from the plant. As a living specimen, it conducts the regular reactions of photosynthesis and respiration, in significantly lower rates than compared to the living plant itself.

The longevity of the vase life of cut flowers depends on the following factors: (1) inability of stems to absorb water due to xylem blockage, (2) excessive water loss from the cut flower, (3) short supply of carbohydrate to support respiration, (4) diseases, and (5) ethylene gas.

To prolong the vase life of fresh cut flowers, many preservatives have been used in the floral industry. In general, preservatives have three main functions: (1) provide carbohydrates to cause the respiration process, (2) supply bactericide to prevent microbial growth and blockage of the water-conducting cells in stems, and (3) acidify the storage solution for increasing the water flow through the stem. Using a floral preservative significantly increases vase life of some flowers.

The effectiveness of preservatives depends not only upon the amount of light and temperature, but also upon the amount and quality of water, types of flowers and vase load (number of flowers per vase or number of bouquets per bucket). Respiration and photosynthesis may be controlled by temperature and light. In this invention, the respiration and photosynthesis rate are controlled during the storage life through prevention of a potassium deficit.

Potassium is a macro-element actively involved in the photosynthesis and respiration processes. Potassium regulates the rate of photosynthesis by its reaction with adenosine triphosphate (ATP). In addition, potassium plays a key role in transporting water and nutrients through cells. Plants depend upon potassium to regulate the opening and closing of stomates, the pores through which leaves exchange carbon dioxide ($CO_2$), water vapor, and oxygen ($O_2$) with the atmosphere. Proper functioning of stomates is essential for photosynthesis, water and nutrient transport, and plant cooling. When potassium moves into the cells around the stomates, the cells accumulate water and swell, causing the pores to open and allowing gases to move freely in and out. When water supply is short, potassium is pumped out of the cells. If the potassium supply is inadequate, plants are less able to absorb water.

Potassium's ability to stimulate the biochemical processes, including photosynthesis and respiration, may be used as a method of energy boost in cut flowers. Potassium injection activates sugar production by photosynthesis.

Potassium may be added to the solution in the form of a potassium salt. Preferably, a potassium based electrolyte is used to provide potassium ions as a nutrient source for cut flowers. More preferably, potassium chloride is used to provide potassium ions as a nutrient source for cut flowers.

Electrochemically processed potassium chloride solution possesses three main properties required for the fresh cut flowers preservative: (1) it supplies biocide to prevent the microbial growth; (2) it provides optimal pH storage conditions; and (3) it boosts the energy in cut flowers, all of which result in better respiration and photosynthesis during storage life and vase life. Potassium chloride solution processed through a diaphragm based electrolytic cell, enriched with hypochlorous acid and dissolved oxygen at a pH range, preferably, between 2.5 and 8 and, more preferably, between 3 and 6, and TDS (total dissolved solids) level, preferably, below 9 g/L and, more preferably, below 2.5 g/L, may be used as a universal preservative for cut flowers at the post harvesting and storage life stages.

The energy boost is often associated with the sugar placed in floral preservatives. In reality, not all cut flowers benefit from sugar. If the sugar concentration is too high, the flowers may be damaged. The alternative of using potassium as a method of energy boost increases the vase life longevity.

In addition to using potassium in the solution, the combined effect of using hypochlorous acid and controlling pH in the electrochemical treatment of the solution produces effective microbial control, i.e., prevents microbial growth. Further, the use of electrochemically treated potassium chloride solution enriched with hypochlorous acid and dissolved oxygen diminishes the negative effect of temperature fluctuation and water stress of cut flowers not only during storage life, but during vase life as well, no matter if the flowers are stored in commercial preservative or regular tap water. Hypochlorous acid is preferably supplied in a nondissociated form.

Electrochemically treated potassium chloride solution enriched with hypochlorous acid and dissolved oxygen not only provides better quality of water but also provides better quality of sterns and flowers. All types of flowers, including mixed bouquets, benefit from the solution.

The composition of the electrochemically treated solution comprises water, potassium chloride, hypochlorous acid, and dissolved oxygen. In one embodiment, the composition comprises at least 99.5% by weight water, 0.3% by weight or less potassium chloride, 0.01% by weight or less hypochlorous acid, and 0.001% by weight or less dissolved oxygen.

In another embodiment, the composition comprises at least 99.5% by weight water, 0.3% by weight or less potassium chloride, 0.01% by weight or less hypochlorous acid, and 0.002% by weight or less dissolved oxygen.

In one preferred embodiment, the solution also has a specific conductivity, or salinity, of about 0.2-18 mS (milisiemens) and is produced at an optimized pH of about 2.5-10 and concentration of 5-600 ppm Available Free Chlorine (AFC) equivalent. In another preferred embodiment, the solution also has a specific conductivity of 0.2-18 mS and is produced at an optimized pH of about 2.5-8 and concentration of 5-600 ppm Available Free Chlorine (AFC) equivalent. AFC equivalent refers to a measure of all oxidants. In a more preferred embodiment, the solution has a specific conductivity of 0.2-6 mS and is produced at an optimized pH of about 3-6 and concentration of 25-120 ppm AFC equivalent. In a most preferred embodiment, the solution has a specific conductivity of 2-4 mS and is produced at an optimized pH of about 4-5 and concentration of 50 ppm AFC equivalent. In the solution, pH is limited by potassium content in the low range and by ionization form in the high range. Salinity is limited by the flowers' sensitivity.

The components of the solution may be processed through an electrolytic cell to produce the electrochemically treated solution. Devices, such as the Sterilox® 2200 may be used for the electrochemical treatment; however, any other device with an electrolytic cell may be used.

The invention also provides a method of extending cut flower and plant life by providing an electrochemically treated aqueous solution having potassium, hypochlorous acid and dissolved oxygen and immersing a stem in the electrochemically treated aqueous solution. No special handling or storage techniques are necessary. Storage of the flowers using this method may be done in any container, including vases and buckets at retailers, wholesalers, and homes. The method may also include recutting of the cut flowers and replacing the solution or mixing the solution with water, the same solution, or other solutions. In addition, other parts of the flower, besides the stem, may be dipped or soaked in the solution.

The benefits of this method include reducing cloudiness and slime formation in the solution, controlling unpleasant odor formation in the stem and any flower attached to the stem, extending storage life of the stem and any flower attached to the stem, and limiting mold growth and slime formation on the stem. The storage life may be extended upwards of 15-20 days or 25 days or possibly more, depending upon the conditions where the stems and flowers are stored and how soon they are placed in the solution.

The following examples are presented to illustrate the invention. In the examples, the following terms have been used:

"(A) solution" means a solution generated using potassium chloride as the electrolyte having potassium chloride at 50 ppm of AFC, a pH range of 4-5, and a salinity range of 2-4 mS.

"(B) Comparative solution" means water with a solid granulated product used for floral preservation that was prepared following manufacturers instructions.

"Unsellable" means that the flowers lost their leaves and/or were wilted.

"Storage life" means the time the flowers are kept in cold storage at a retailer or wholesaler.

"Home life" means the time a flower lasts in customer's home.

Test Methods

AFC level in water and floral solutions was measured using a HACH® test kit (Hach Company, Loveland, Colo.).

Conductivity was measured with an Oakton® conductivity meter (Oakton Instruments, Vernon Hills, Ill.).

Dissolved oxygen was measured with a HACH® LDO meter (Hach Company, Loveland, Colo.) as an express method for evaluation of Biochemical Oxygen Demand in used solutions and dissolved oxygen in ready to use solutions.

pH was measured with an Oakton® pH meter (Oakton Instruments, Vernon Hills, Ill.).

Turbidity was measured using the HACH® DR4000/UV spectrophotometer and HACH® turbidity method 3750 (Hach Company, Loveland, Colo.).

Water quality was evaluated based on two parameters: turbidity and level of dissolved oxygen.

EXAMPLES

Example 1

Effectiveness of Solution with Mixed Bouquets

Laboratory studies were performed to compare the effectiveness of an optimized electrochemically treated solution against the solid granulated product during storage and home life of mixed bouquets and maintaining the clarity of the bucket solution.

Run 1

Four vases were filled with 1.5 liters of either (A) solution generated using potassium chloride as the electrolyte or (B) Comparative solution. Initially, mixed flower bouquets were trimmed by one inch from their stems, and 2 or 3 15-stem bouquets were placed into the vases. A total number of stems were varied between 30 and 45 per each vase for each test solution type. One week later, the bouquets were arranged by placing into (A) solution, (B) Comparative solution and (C) tap water, one bouquet per vase.

Observations were documented on appearance and liveliness of flowers and their stems and clarity of solution. Individual flowers were removed from testing after being deemed "unsellable." Turbidity, conductivity, dissolved oxygen and pH of solution, as well as total amount of intake water per vase, was also measured.

Flowers were topped up every three days with either water in the (B) Comparative solution treated flowers or with (A) solution in the (A) solution treated flowers during a first stage and with tap water in the (B) Comparative solution treated flowers and (C) tap water treated flowers or with (A) solution in the (A) solution treated flowers during a second stage.

Run 2

Five vases were filled with 1.5 liters of either (A) solution or (B) Comparative solution. Initially, mixed flower bouquets were trimmed by one inch from their stems, and 1, 2 or 3 15-stem bouquets were placed into the vases. A total number of stems were varied between 15 and 45 per each vase for each test solution type. One week later, the bouquets were arranged by placing into tap water, one bouquet per vase.

Observations were documented on appearance and liveliness of flowers and their stems and clarity of solution. Individual flowers were removed from testing after being deemed "unsellable." Turbidity, conductivity, dissolved oxygen and pH of solution, as well as total amount of intake water per vase, was also measured.

Flowers were topped up every three days with either water in the (B) Comparative treated flowers or with (A) solution in the (A) solution treated flowers during a first stage and with tap water during a second stage.

Results

The shelf life of flowers, contained at room temperature during storage life and home-life, was measured over 14 days. Most of the (B) Comparative solution treated during storage life flowers died within the 7 days of home life (over 14 days of trial). The quality of stems in control samples was observed for either (A) solution or (B) Comparative solution treatment. Flowers treated with (A) solution showed no mold growth on their stems throughout the trial and also demonstrated low turbidity.

In contrast, (B) Comparative solution treated flowers showed cloudiness after 3 days of storage life and also visible mold was observed on the stems by the 5th day of vase life. Furthermore, significantly higher turbidity units were observed in the floral food solutions during storage life in both trials.

(A) solution demonstrated better performance under over-stressed conditions by means of temperature (78° F. or 25° C.) and flowers load per vase. Flowers stored in (A) solutions during storage life showed better appearance during home life no matter how they were treated during that stage.

In contrast, (B) Comparative solution treated flowers showed cloudiness after 3 days of storage in both high and low loaded vases. Furthermore, significantly higher turbidity units were observed in the floral food solutions at all stages. Stems of flowers demonstrated slime accumulation by the 5$^{th}$ day of both trials. Significant mold growth was observed by the end of the home life stage.

Overall, (A) solution provided better "home life" than (B) Comparative solution, controlled cloudiness and slime formation of the solution and on the stems, protected stems from rotting and mold growth during home life, and controlled unpleasant odor formation in mixed bouquets during home life.

Example 2

Effectiveness of Solution with Cut Roses

Laboratory studies were performed to compare the effectiveness of an optimized electrochemically treated solution against the solid granulated product in extending the shelf life of cut roses and carnations and maintaining the clarity of a bucket solution.

Example 2.1

Roses

Six vases were filled with 1.5 liters of either (A) solution generated using potassium chloride as the electrolyte or (B) Comparative solution. Red roses were trimmed by one inch from their stems and 25 roses were placed into the vases. A total of 75 roses were used for each test solution type. Observations were documented on appearance and liveliness of roses and clarity of solution. Individual roses were removed from testing after being deemed "unsellable." Turbidity, conductivity, dissolved oxygen and pH of solution were also measured. Flowers were topped up every two days with either water in the (B) Comparative solution treated flowers or with (A) solution in the (A) solution treated flowers.

Results

The shelf life of roses at room temperature was measured over 15 days. All control sample roses died within the 15 days. As shown in Table. 1, equivalent shelf life of roses was observed for either (A) solution or (B) Comparative solution treatment. Roses stored in (A) solutions showed no cloudiness throughout the trial and also demonstrated low turbidity, as shown in Table 2.

In contrast, (B) Comparative solution treated roses showed cloudiness after 2 days of storage, as shown in Table 2. Visible biofilm slime was observed on the sides of the vases by the 5th day and accumulated in the vases throughout the rest of the trial. Furthermore, Table 2 shows that significantly higher turbidity units were observed in the (B) Comparative solutions.

TABLE 1

Shelf-life of Roses Treated with Either Sterilox or Floral Food

| | Number of Stems | |
|---|---|---|
| Days | Floral Food | Sterilox Solution |
| 0 | 25 | 25 |
| 1 | 25 | 25 |
| 3 | 25 | 25 |
| 6 | 25 | 25 |
| 9 | 16 | 17 |
| 12 | 15 | 13 |
| 15 | 9 | 8 |

TABLE 2

Turbidity of Roses Treated with Either Sterilox or Floral Food

| | Average Turbidity (Units) | |
|---|---|---|
| Days | Floral Food | Sterilox Solution |
| 0 | 0 | 0 |
| 1 | 10 | 0 |
| 3 | 16 | 0 |
| 6 | 16 | 0 |
| 9 | 23 | 3 |
| 12 | 23 | 3 |
| 15 | 32 | 3 |

Example 2.2

Carnations

Four Vases were filled with 1.5 liters of either (A) solution generated using potassium chloride as the electrolyte or (B) Comparative solution. Carnations were trimmed by one inch from their stems and either 48 carnations (trial 1) or 34 carnations (trial 2) were placed into the vases. A total of 96 carnations (trial 1) or 68 carnations (trial 2) were used for each solution type. Observations were documented on appearance and liveliness of carnations and clarity of solution. Individual carnations were removed from testing after being deemed "unsellable." Turbidity, conductivity, dissolved oxygen and pH of solution were also measured. Flowers were topped up every two days with either water in the (B) Comparative solution treated flowers or with (A) solution in the (A) solution treated flowers.

Results

The shelf life of carnations at room temperature was measured over either 14 or 17 days. As shown in Tables 3 and 5, equivalent shelf life of carnations was observed for either (A) solution or (B) Comparative solution treatment in both trials. Carnations stored in (A) solution in both trials showed no cloudiness or slime accumulation, and low turbidity readings were measured for both trials, as shown in Tables 4 and 6.

In contrast, (B) Comparative solution treated carnations showed cloudiness after 2 days of storage, and visible biofilm slime was observed on the sides of the vase after 5 days. Furthermore, significantly higher turbidity units were observed in both trials in the (B) Comparative solutions, as shown in Tables 4 and 6. The stems of the carnations demonstrated slime accumulation by the $5^{th}$ day of both trials.

TABLE 3

Shelf-life of Carnations Treated with Either Sterilox or Floral Food in Trial 1

| | Number of Stems | |
|---|---|---|
| Days | Floral Food | Sterilox |
| 0 | 34 | 34 |
| 1 | 34 | 34 |
| 5 | 34 | 34 |
| 8 | 33 | 33 |
| 11 | 27 | 30 |
| 14 | 25 | 29 |

TABLE 4

Turbidity of Carnations Treated with Either Sterilox or Floral Food in Trial 1

| | Average Turbidity (Units) | |
|---|---|---|
| Days | Floral Food | Sterilox Solution |
| 0 | 0 | 0 |
| 1 | 0.5 | 0 |
| 5 | 5.5 | 0.5 |
| 8 | 3 | 1.5 |
| 11 | 11.5 | 0 |
| 14 | 44 | 6.5 |

TABLE 5

Shelf-life of Carnations Treated with Either Sterilox or Floral Food in Trial 2

| | Number of Stems | |
|---|---|---|
| Days | Floral Food | Sterilox Solution |
| 0 | 45 | 45 |
| 1 | 45 | 45 |
| 3 | 45 | 45 |
| 5 | 45 | 45 |
| 7 | 45 | 45 |
| 10 | 45 | 43 |
| 14 | 41 | 41 |
| 17 | 32 | 38 |

TABLE 6

Turbidity of Carnations Treated with Either Sterilox or Floral Food in Trial 2

| | Average Turbidity (Units) | |
|---|---|---|
| Days | Floral Food | Sterilox Solution |
| 0 | 0 | 0 |
| 1 | 8 | 1 |
| 3 | 8 | 2.5 |
| 5 | 12 | 1.5 |
| 7 | 9 | 3 |
| 10 | 95 | 6.5 |
| 14 | 190 | 5.5 |
| 17 | 213 | 13 |

While the invention has been described in detail and with reference to specific embodiments thereof, it will be apparent to one skilled in the art that various changes and modifications can be made therein without departing from the spirit and scope thereof. For example, the electrochemically treated solution may comprise additional components added before or after electrolysis to achieve certain properties. These additional components may include sugars, salts, surfactants, pH stabilizers, bactericides, fungicides, nutrients, and other preservatives. Thus, it is intended that the invention covers the modifications and variations of this invention provided they come within the scope of the appended claims and their equivalents.

The invention claimed is:

1. A solution for cut flower and plant preservation consisting of:
   at least 99.5% by weight water;
   an effective amount of potassium chloride;
   an effective amount of but no more than 0.01% by weight hypochlorous acid, wherein the hypochlorous acid is supplied in an undissociated form; and
   an effective amount of dissolved oxygen,
   wherein the solution is electrochemically treated, has a total dissolved solids level of no more than 9 g/L, has a conductivity of 0.2-18 mS, has 5-600 ppm of available free chlorine equivalent, and has a pH of 4 to 6.

2. The solution of claim 1 wherein the total dissolved solids level is no more than 2.5 g/L.

3. The solution of claim 2 wherein the conductivity is 0.2-6 mS.

4. The solution of claim 1 wherein the pH is 4 to 5.

5. The solution of claim 1 wherein the available free chlorine equivalent is 25-100 ppm.

6. The solution of claim 1 wherein the solution has:
the effective amount of at least 99.5% by weight water;
the effective amount of potassium chloride is no more than 0.3% by weight;
the effective amount of hypochlorous acid is no more than 0.01% by weight; and
the effective amount of dissolved oxygen is but no more than 0.001% by weight.

7. A solution for cut flower and plant preservation consisting of:
at least 99.5% by weight water;
an effective amount of but no more than 0.25% by weight potassium chloride;
an effective amount of but no more than 0.01% by weight hypochlorous acid; and
an effective amount of but no more than 0.001% by weight dissolved oxygen,
wherein the solution is electrochemically treated and has a pH of 4 to 6 and a conductivity of 0.2-6 mS.

8. A method of extending cut flower and plant life comprising:
providing an electrochemically treated aqueous solution wherein the solution consists of potassium chloride, hypochlorous acid, dissolved oxygen, has a total dissolved solids level of no more than 9 g/L, has a conductivity of 0.2-18 mS, has 5-600 ppm of available free chlorine equivalent, and a pH of 4 to 6; and
immersing a stem in the electrochemically treated aqueous solution.

9. The method of claim 8 wherein the pH is 4 to 5.

10. The method of claim 8 wherein the total dissolved solids level is no more than 2.5 g/L.

11. The method of claim 10 wherein the conductivity is 0.2-6 mS.

12. The method of claim 8 wherein the available free chlorine equivalent is 25-125 ppm.

13. The method of claim 8 wherein the solution has:
the effective amount of at least 99.5% by weight water;
the effective amount of potassium chloride is no more than 0.3% by weight;
the effective amount of hypochlorous acid is no more than 0.01% by weight; and
the effective amount of dissolved oxygen is no more than 0.001% by weight.

14. The method of claim 8 wherein the step of immersing further comprises:
reducing turbidity and slime formation in the solution;
preserving the life of the stem and any flower attached to the stem upwards of 15 to 20 days; and
limiting mold growth and slime formation on the stem.

15. The solution of claim 7 wherein the effective amount of the potassium chloride is no more than 0.2% by weight, the pH is 4 to 5, and the conductivity is 0.4-4.4 mS.

16. The method of claim 8 wherein the pH is 4 to 5, the conductivity is 0.4-4.4 mS,
the effective amount of water is at least 99.5% by weight,
the effective amount of potassium chloride is no more than 0.2% by weight potassium chloride;
the effective amount of hypochlorous acid is no more than 0.01% by weight, and
the effective amount of dissolved oxygen is no more than 0.001% by weight.

\* \* \* \* \*